_United States Patent_ [19]

Warchol

[11] Patent Number: 4,818,105
[45] Date of Patent: Apr. 4, 1989

[54] BURNER FOR FLAME PHOTOMETRIC DETECTOR

[75] Inventor: Andrew M. E. Warchol, Media, Pa.

[73] Assignee: Hewlett-Packard Company, Palo Alto, Calif.

[21] Appl. No.: 99,435

[22] Filed: Sep. 21, 1987

[51] Int. Cl.[4] ............................................ G01N 21/72
[52] U.S. Cl. ...................................... 356/315; 356/417
[58] Field of Search ................................ 356/315, 417

[56] References Cited

U.S. PATENT DOCUMENTS

| | | | |
|---|---|---|---|
| 2,058,522 | 10/1936 | Smyly | 73/190 |
| 2,532,687 | 12/1950 | Weichselbaum | 356/417 |
| 2,562,874 | 7/1951 | Weichselbaum | 356/315 |
| 2,602,142 | 7/1952 | Meloy . | |
| 2,664,779 | 1/1954 | White | 356/417 |
| 2,730,005 | 1/1956 | Vonnegut . | |
| 2,750,512 | 6/1956 | Meloy . | |
| 2,990,748 | 7/1961 | Vallee et al. | 356/315 |
| 2,991,158 | 7/1961 | Harley et al. . | |
| 3,038,069 | 6/1962 | Tuller . | |
| 3,039,856 | 6/1962 | McWilliams . | |
| 3,133,201 | 5/1964 | Rock | 250/226 |
| 3,140,919 | 7/1964 | Gallaway et al. . | |
| 3,169,832 | 2/1965 | Gallaway et al. . | |
| 3,198,062 | 8/1965 | Chaffee | 356/315 |
| 3,211,050 | 10/1985 | Pelavin | 350/417 |
| 3,213,747 | 10/1965 | Van Smissen . | |
| 3,243,700 | 3/1966 | McAvoy et al. | 324/58 |
| 3,249,754 | 5/1966 | Laikin et al. . | |
| 3,345,537 | 10/1967 | Spencer | 315/85 |
| 3,374,436 | 3/1968 | Thiess | 325/336 |
| 3,486,827 | 12/1969 | Binek et al. | 356/417 |
| 3,489,498 | 1/1970 | Brody et al. | 356/417 |
| 3,493,753 | 2/1970 | Stowe . | |
| 3,617,734 | 11/1971 | Chaudet . | |
| 3,645,627 | 2/1972 | Brody et al. | 356/417 |
| 3,692,415 | 9/1972 | Shiller | 356/417 |
| 3,743,425 | 7/1973 | Jobe | 356/315 |
| 3,807,863 | 4/1974 | Raillere et al. | 356/417 |
| 3,860,345 | 1/1975 | Raillere et al. | 356/417 |
| 3,970,394 | 7/1976 | Stanton | 250/227 |
| 4,119,404 | 10/1978 | Price | 356/417 |
| 4,234,257 | 11/1980 | Carter et al. | 356/417 |

OTHER PUBLICATIONS

Bulletin Number 151-A, The Weichselbaum-Varney Universal Spectrophotometer, 1950, pp. 1-7.

_Primary Examiner_—F. L. Evans
_Attorney, Agent, or Firm_—Jeffery B. Fromm; Richard F. Schuette

[57] ABSTRACT

A burner for a flame photometric detector includes a stainless steel housing having a passage therethrough; a stainless steel burner tube extending through the passage and having a flame holder at one end; and at least one stainless steel inlet tube extending through the housing for admitting a support gas to the burner. The burner tube and inlet tube are brazed to the housing to form a unitary device having no sealing rings which can degrade and leak. A transfer line is connected to one end of the burner to conduct the material to be tested to the burner. The transfer line includes a fused silica tube surrounded by a stainless steel outer tube.

13 Claims, 1 Drawing Sheet

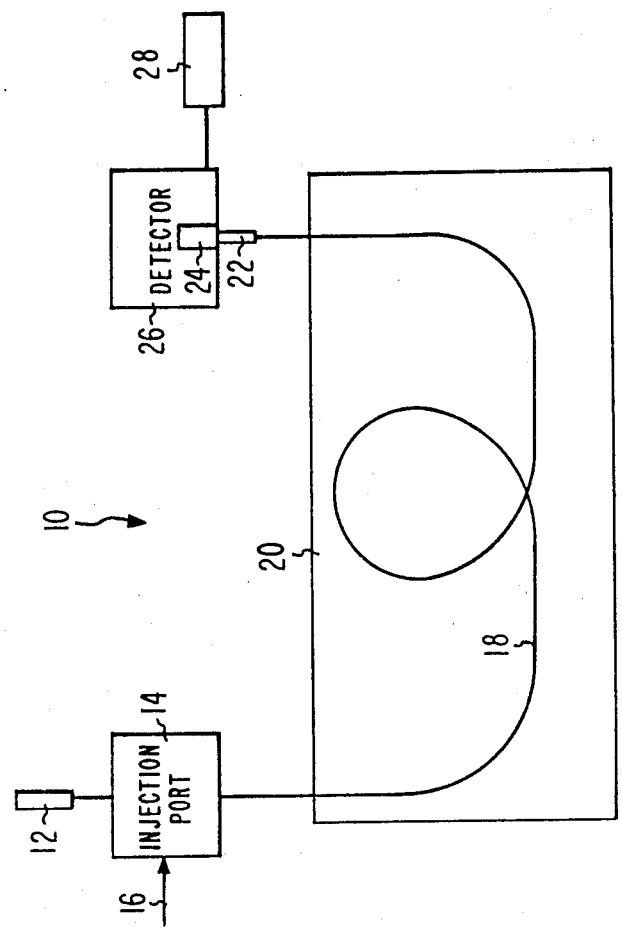
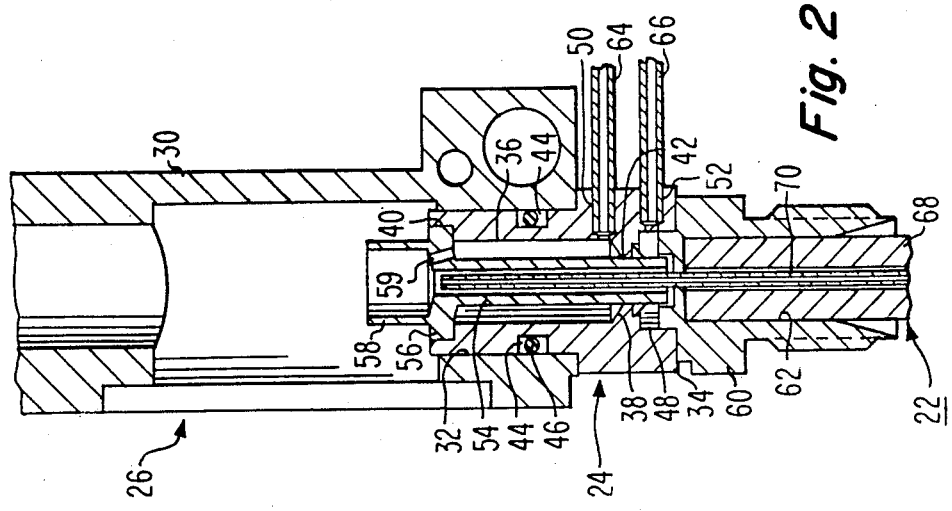

BURNER FOR FLAME PHOTOMETRIC DETECTOR

FIELD OF THE INVENTION

The present invention relates to an improved design of the burner of a photometric detector, and more particularly to a design which eliminates sealing rings between the parts of the burner and which includes an improved transfer line.

BACKGROUND OF THE INVENTION

Gas chromatrographs have been used for detecting certain elements in materials. As described in U.S. Pat. No. 3,489,498 to S. S. Brody et al, entitled FLAME PHOTOMETRIC DETECTOR WITH IMPROVED SPECIFICITY TO SULFUR AND PHOSPHORUS, issued Jan. 13, 1970, such devices generally include a sample injector, a flame photometric detector, and a chromatographic column connecting the sample injector to the flame photometric detector. One problem with the prior art flame photometric detectors is that the burner is generally formed of several parts which are sealed together either by metal-to-metal seals or sealing rings. It has been found that at the temperatures at which the burner operates, the seals tend to degrade and leak causing long term drift of sensitivity and noise. Also, the material of the sealing rings tend to outgas contaminates into the device resulting in high baseline noise.

Another problem arises from the sample transfer line, which have been made of stainless steel or glass lined stainless steel. The transfer line is used to maximize detector signal to noise ratio by thermally isolating the photomultiplier tube in the detector from the hot detector heated zones and chromatographic oven. However, the longer the transfer line, which improves the isolation, the more difficult it is to maintain isothermal temperature, and any hot or cold spots can result in significant loss or degradation of sample compounds. Stainless steel or glass lined stainless steel have been found to have more reactive sites and are therefore much more vulnerable to hot and cold spots which can degrade the sample material.

Therefore, it would be desirable to have a burner which eliminates the problems caused by sealing rings between the parts of the burner, and a transfer line which minimizes degradation of the sample material.

SUMMARY OF THE INVENTION

A burner for a flame photometric detector includes a housing having a passage therethrough, a burner within the passage in the housing, and at least one gas inlet tube extending through the wall of the housing into the passage. The housing, burner and inlet tube are brazed to the housing to form a tightly sealed integral unit. The transfer line extending into the housing is a fused silica column within a stainless steel tube.

BRIEF DESCRIPTION OF THE DRAWINGS

FIG. 1 is a schematic view of a gas chromatograph which can utilize the burner of the present invention; and FIG. 2 is a sectional view of the burner and a portion of the transfer line of the present invention.

DESCRIPTION OF THE PREFERRED EMBODIMENT

Referring to FIG. 1, a typical gas chromatograph is generally designated as 10. Gas chromatograph 10 includes a sample holder 12 connected to an injection port 14. A carrier gas inlet tube 16 also extends into the injection port 14 to admit an inert carrier gas, such as nitrogen, argon or helium, into the injection port 14. The injection port 14 is connected to a chromatographic column 18 which passes through an oven 20. The column 18 is connected by a transfer line 22 to the burner 24 of a flame photometric detector 26. The detector 26 generally includes herein a photodetector, not shown, of the type described in U.S. Pat. No. 3,489,498 to S. S. Brody et al which is connected to a recorder 28.

Referring to FIG. 2, the photometric detector 26 includes a burner chamber 30 having a passage 32 therethrough into which the burner 24 fits. The burner 24 includes a cylindrical housing 34 of stainless steel. A passage 36 extends longitudinally through the housing 34 from its top end to a bottom wall 38. A recess 40 is in the wall of the passage 36 at the top end of the housing 34. An opening 42, smaller in diameter than the passage 36, extends through the bottom wall 38 to the passage 36. An annular groove 44 is in the outer surface of the housing 34 and is adapted to receive a sealing ring 46, preferably of a perfluoro-elastomer, such as DuPont Kalrez. A recess 48 is in the bottom end of the housing 34 and has an inner diameter larger than that of the opening 42 in the bottom wall 38. A first inlet port 50 extends radially through the housing 34 into the passage 36 adjacent the bottom wall 38. A second inlet port 52 extends radially through the housing 34 into the recess 48.

A cylindrical burner tube 54 extends along the passage 36 and through the opening 42 in the bottom wall 38. The outer diameter of the burner tube 54 is equal to the inner diameter of the opening 42 so that the burner tube 54 has a tight fit in the opening 42. The burner tube 54 has a radially outwardly extending flange 56 at its top end which fits tightly within the recess 40 in the upper end of the passage 36. A cylindrical flame holder 58 projects upwardly from the flange 56 and has an inner diameter larger than that of the burner tube 54. A plurality of openings 59 extend through the flange 56 from the space around the burner tube 54 to the interior of the flame holder 58. The burner tube 54, flange 56 and flame holder 58 are made of stainless steel.

A cylindrical fitting 60 of stainless steel is secured to the bottom end of the burner housing 34. The fitting 60 has a passage 62 therethrough which opens into the burner tube 54. However, the top end of the fitting 60 is spaced from the bottom end of the burner tube 54 so as to provide a passage therebetween. The bottom end of the outer surface of the fitting 60 is threaded. A first inlet tube 64 of stainless steel has an end fitting tightly in the first inlet port 50. A second inlet tube 66 of stainless steel has an end fitting tightly in the second inlet port 52. The first inlet tube 64 is adapted to admit air or oxygen to the burner to burn the sample material, and the second inlet tube 66 is adapted to admit hydrogen and nitrogen into the system.

The burner tube 54, fitting 60 and inlet tubes 64 and 66 are all brazed to the burner housing 34, preferably by vacuum furnace brazing. This provides a unitary device in which the parts are tightly secured together by means which will withstand high temperatures and which does not include any sealing rings.

The transfer line 22 is secured in the passage 62 in the fitting 60. The transfer line 22 includes an outer tube 68 of stainless steel which fits in the passage 62 and an inner tube 70 of fused silica. The fused silica inner tube 70 has a relatively large inner diameter, about 900 microns. The fused silica inner tube 7 extends beyond the end of the stainless steel outer tube 68 through the burner tube 54 and up to the flame holder 58. The fused silica inner tube 70 is inert and results in much less degradation of the sample material being tested. Also, the fused silica inner tube 70 can extend directly up to the base of the flame formed in the flame holder 58 so that the sample material is delivered directly into the flame. This provides for maximum detector sensitivity and minimum sample degradation. In addition, since the fused silica inner tube has a large internal diameter, it allows columns having a large range of diameters to be coupled to the detector.

In the flame photometric detector 26 of the present invention, the burner 24 is of unitary construction which can be easily inserted or removed from the burner chamber 30. The burner 24 is sealed to the burner chamber 30 by the sealing ring 46 which is of a material which will withstand the high temperatures of the burner. Also, since the parts of the burner are all brazed together there are no sealing rings which can degrade and leak or which give off undesirable contaminants. The transfer line being of fused silica minimizes the degradation of the sample material due to hot and cold spots in the transfer line and allows the sample material to be delivered directly into the flame. Thus, there is provided by the present invention a burner and transfer line for a flame photometric detector which greatly improves the operation of the detector.

The present invention may be embodied in other specific forms without departing from the spirit or essential attributes thereof and, accordingly, reference should be made to the appended claims, rather than to the foregoing specification, as indicating the scope of the invention.

I claim:

1. A burner for a flame photometric detector comprising:
    a housing having a passage therethrough, said housing having a wall adjacent one end across the passage and an opening through the wall to the passage which opening is smaller in diameter than the passage, and a recess at the other end of the housing which is larger in diameter than the passage
    a burner within said passage in the housing, said burner including a cylindrical tube extending through the passage and fitting tightly in the opening in the wall, a radially outwardly extending flange fitting tightly in the recess at the other end of the housing, and a cylindrical flame holder projecting from the flange, and
    at least one gas inlet tube extending through the wall of the housing into the passage;
    said housing, burner, and inlet tube all being of stainless steel and the burner and inlet tube being brazed to the housing to form a tightly sealed integral unit.

2. A burner in accordance with claim 1 including an inlet port extending radially through the housing into the passage and the inlet tube fits tightly in said inlet port.

3. A burner in accordance with claim 2 in which the flange of the burner has a passage therethrough from the space between the burner tube and the housing and the interior of the flame holder.

4. A burner in accordance with claim 3 including a recess in the one end of the housing adjacent the wall of a diameter greater than that of the opening in the wall, a second inlet port extending radially through the housing into said recess and a second stainless steel inlet tube fitting in said second inlet port and brazed to said housing.

5. A burner in accordance with claim 4 including a stainless steel fitting secured and brazed to the one end of the housing and having a passage therethrough opening into the burner tube.

6. A burner in accordance with claim 5 including a transfer line secured in the passage in the fitting, said transfer line having an outer tube of stainless steel and an inner tube of fused silica.

7. A burner in accordance with claim 6 in which the fused silica inner tube extends through the burner tube to the flame holder.

8. A burner in accordance with claim 1 including a transfer line secured to said burner housing to conduct the material being tested to the burner, said transfer line including a tube of fused silica.

9. A burner in accordance with claim 8 in which the transfer line includes a stainless steel tube surrounding the fused silica tube.

10. A burner for a flame photometric detector comprising:
    a housing having a passage therethrough, said housing having a wall adjacent one end across the passage and an opening through the wall to the passage which opening is smaller in diameter than the passage;
    a burner within said passage in the housing, said burner fitting tightly in the opening in the wall; and
    at least one gas inlet tube extending through the wall of the housing into the passage;
    said housing, burner, and inlet tube all being of stainless steel and the burner and inlet tube being brazed to the housing to form a tightly sealed integral unit.

11. A burner in accordance with claim 10 wherein said burner includes a burner tube extending through the passage of the housing and including a stainless steel fitting secured and brazed to the housing and having a passage therethrough opening into the burner tube.

12. A burner for a flame photometric detector comprising:
    a housing having a passage therethrough;
    a burner tube within said passage in the housing;
    at least one gas inlet tube extending through the wall of the housing into the passage of said housing; and
    a fitting having a passage therethrogh opening into the burner tube,
    said housing, burner tube, inlet tube and fitting all being of stainless steel and the burner tube, inlet tube and fitting being brazed to the housing to form a tightly sealed integral unit.

13. A burner in accordance with claim 12 including a transfer line secured to said fitting to conduct the material being tested to the burner, said transfer line including a tube of fused silica.

* * * * *